(12) United States Patent
Bertram et al.

(10) Patent No.: US 10,628,963 B2
(45) Date of Patent: Apr. 21, 2020

(54) AUTOMATIC DETECTION OF AN ARTIFACT IN PATIENT IMAGE

(71) Applicant: Brainlab AG, Munich (DE)

(72) Inventors: Pascal Bertram, Munich (DE); Birte Domnik, Munich (DE); Elisa Garcia Corisco, Munich (DE)

(73) Assignee: Brainlab AG, Munich (DE)

( * ) Notice: Subject to any disclaimer, the term of this patent is extended or adjusted under 35 U.S.C. 154(b) by 135 days.

(21) Appl. No.: 16/066,551

(22) PCT Filed: Feb. 29, 2016

(86) PCT No.: PCT/EP2016/054231
§ 371 (c)(1),
(2) Date: Jun. 27, 2018

(87) PCT Pub. No.: WO2017/148502
PCT Pub. Date: Sep. 8, 2017

(65) Prior Publication Data
US 2019/0012805 A1    Jan. 10, 2019

(51) Int. Cl.
*G06T 7/73* (2017.01)
*A61B 6/00* (2006.01)
(Continued)

(52) U.S. Cl.
CPC ............. *G06T 7/74* (2017.01); *A61B 6/032* (2013.01); *A61B 6/5264* (2013.01);
(Continued)

(58) Field of Classification Search
CPC .. G06T 7/74; G06T 7/174; G06T 7/90; G06T 7/254; G06T 2207/10081;
(Continued)

(56) References Cited

U.S. PATENT DOCUMENTS

| | | | | |
|---|---|---|---|---|
| 4,953,087 A | * | 8/1990 | Crawford | G01R 33/56 345/419 |
| 5,357,549 A | * | 10/1994 | Maack | H04N 1/4072 378/62 |

(Continued)

OTHER PUBLICATIONS

Ehrhartdt, et al., "An optical flow based method for improved reconstruction of 4D CT data sets acquired during free breathing", Medical Physics, AIP, Melville, NY, US. vol. 34 No. 2, Jan. 29, 2007. pp. 711-721, XP012103314, ISSN: 0094-2405.

(Continued)

*Primary Examiner* — Juan A Torres
(74) *Attorney, Agent, or Firm* — Tucker Ellis LLP

(57) ABSTRACT

A medical data processing method and system determines the position of an artifact in patient image data describing a set of tomographic slice images of an anatomical structure of a patient. The images are described by color Values. Color value difference data describing differences in color values for image elements in adjacent slice images is determined. At least one of positive or negative difference data, describing a subset of the differences and consisting of differences having a positive or negative value are determined. Smoothed difference data describing a smoothing of the differences contained in the positive or negative difference data are determined and, based on the positive or negative difference data and the smoothed difference data, artifact position data is determined describing the position of an artifact in the patient image data.

12 Claims, 14 Drawing Sheets

(51) Int. Cl.
  *G06T 7/254* (2017.01)
  *G06T 7/174* (2017.01)
  *G06T 7/90* (2017.01)
  *A61B 6/03* (2006.01)

(52) U.S. Cl.
  CPC ............ *A61B 6/5288* (2013.01); *G06T 7/174* (2017.01); *G06T 7/254* (2017.01); *G06T 7/90* (2017.01); *A61B 6/486* (2013.01); *G06T 2207/10076* (2013.01); *G06T 2207/10081* (2013.01); *G06T 2207/20128* (2013.01); *G06T 2207/20221* (2013.01); *G06T 2207/20224* (2013.01); *G06T 2207/30061* (2013.01)

(58) Field of Classification Search
  CPC . G06T 2207/20128; G06T 2207/20221; G06T 2207/10076; G06T 2207/20224; G06T 2207/30061; A61B 6/5288; A61B 6/032; A61B 6/5264; A61B 6/486
  USPC .......................................................... 382/130
  See application file for complete search history.

(56) References Cited

U.S. PATENT DOCUMENTS

| | | | | |
|---|---|---|---|---|
| 5,703,965 A * | 12/1997 | Fu | ............................ | G06T 9/007 382/232 |
| 7,653,252 B2 * | 1/2010 | Hernandez | ............ | H04N 19/115 382/128 |
| 2002/0031277 A1 * | 3/2002 | Lubin | ........................ | G06T 5/50 382/254 |
| 2009/0147908 A1 * | 6/2009 | Garms | .................... | A61B 6/032 378/4 |
| 2010/0061505 A1 | 3/2010 | Wegener et al. | | |
| 2011/0293161 A1 * | 12/2011 | Yi | .......................... | G06T 11/005 382/131 |
| 2017/0156690 A1 * | 6/2017 | Yi | ........................... | A61B 6/032 |

OTHER PUBLICATIONS

Bouilhol et al., "Motion artifact detection in four-dimensional computed tomography images", Journal of Physics: conference Series, Institute of Physics Publishing, Bristol, GB, vol. 489, No. 1, Mar. 24, 2014, p. 12024, XP020259490, ISSN: 1742-6596.
European Patent Office, International Search Report and Written Opinion for corresponding PCT/2016/054321 dated Nov. 17, 2016, pp. 1-12.
Wei et al., "Automated Lung Segmentation and Image Quality Assessment for Clinical 3-D/4-D-Computed Tomography", Medical Imaging and Diagnostic Radiology, 2168-2372 2015 IEEE. Journal of Transitional Engineering in Health and Medicine, vol. 2, 2014, 10 pages, New York, USA.
Georg et al., "Manifold Learning for 4D CT Reconstruction of the Lung" Computer Vision and Pattern Recognition Workshops, 2008. CVPRW'08. IEEE , pp. 1-8.
Han et al., "Characterization and identification of spatial artifacts during 4D-CT imaging", Medical Physics, vol. 38, No. 4, Apr. 2011; American Association of Physicists in Medicine, pp. 1-15.
Wulfhekel et al., "Compilation of a database for illustration and automated detection of 4DCT motion artifacts" University of Medical Center Hamburg-Eppendorf; Radiotherapy & Oncology,vol. 111 (Suppl. 1); ESTRO 33, 2014, EP-1744; p. 5266.
Werner et al., "Reference Geometry-based Detection of (4D-)CT Motion Artifacts: a Feasibility Study" Proc SPIE 9413, S. Ourselin, M.A. Styner (eds.), 94130S, 2015, 1-8 pages including cover page.
Li et al., "Rapid estimation of 4DCT motion-artifact severity based on 1D breathing-surrogate periodicity", Med. Phys. 41 (11), Nov. 2014; pp. 111717-1 thru 111717-9. 10 pages total with cover page.

\* cited by examiner

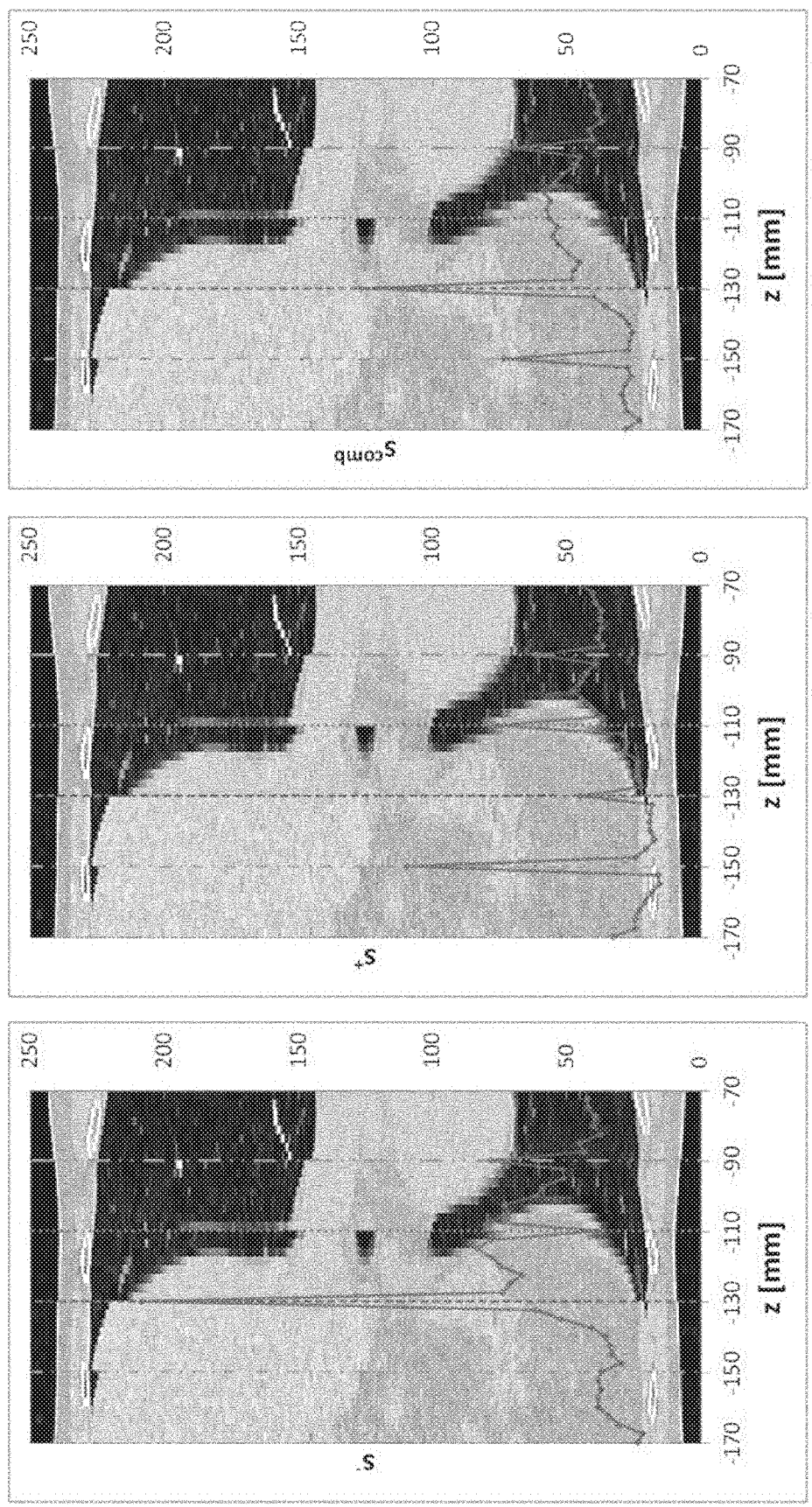

AUTOMATIC DETECTION OF AN ARTIFACT IN PATIENT IMAGE

RELATED APPLICATION DATA

This application is a national phase application of International Application No. PCT/EP2016/054231 filed Feb. 29, 2016 the entire contents of which are incorporated herein by reference and published in the English language.

The present invention relates to a medical data processing method for determining a position of an artifact in patient image data, a corresponding computer program, a non-transitory program storage medium storing such a program and a computer for executing the program, as well as a system for determining a position an artifact in patient image data comprising at least one medical imaging device and such a computer.

TECHNICAL BACKGROUND

Computed tomography (CT) imaging is commonly used for imaging anatomical structures, such as lungs. Recently, four-dimensional computed tomography (4DCT) has been attracting much attention. 4DCT provides valuable information in both spatial and temporal scales. In particular, 4DCT may for example be applied to determine an internal volume of a lung tumor.

Nevertheless, breathing irregularities and heart beating at a different frequency may render 4DCT images distorted. Artifacts (discontinuities in the color values of the images not based on the anatomical structure), in particular motion artifacts, frequently occur in 4DCT. Common motion artifacts are duplicate or missing structures in spatially adjacent transversal slices; incorrect re-use of similar projection data during recon of temporally adjacent 3DCT data; artifacts due to violation of the 4DCT data sufficiency condition/low breathing frequencies.

One approach to determine those artifacts is to simply determine color value differences (for color values associated with Hounsfield unit (HU) values) in the 4DCT images. However, generally the determination of 4DCT motion artifacts by this approach suffers from a low sensitivity. In some instances overlapping-type or duplicate-type artifacts may not be detected at all. Furthermore, analysis of secondary data, for example data describing a respiratory signal, may be necessary.

The present invention allows for a more efficient and more precise determination of a position of an artifact in patient image data.

Aspects of the present invention, examples and exemplary steps and their embodiments are disclosed in the following. Different exemplary features of the invention can be combined in accordance with the invention wherever technically expedient and feasible.

The present invention may be applied in all products used to evaluate whether the information derived from the 4DCT is reliable and useable. The present invention is in particular useful for the following products:

- pre-planning applications analyzing 4DCTs for ExacTrac® gating/tracking (for example, finding anatomical structures whose motion is well correlated with the tumor motion),
- iPlan® RT Dose (radiotherapy dose): 4D treatment planning and also for planning based on the ITV (internal target volume) approach (ITV is the expended CTV (clinical target volume) taking into account the breathing motion, which is usually estimated from 4DCTs).

The advantages of using the present invention in above products are:
- more reliable solutions,
- improved outcome for the patient,
- advantage in the market regarding the ability to evaluate 4DCT quality.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses determining the position of an artifact in tomographic slice images of a patient by determining color value differences for a plurality of pairs of adjacent ones of tomographic slice images. Positive values and negative values in the color value differences are considered separately and compared to reference values, in order to determine the position of an artifact. Thereby, discontinuities (unusually large differences) in color values between neighboring slices may determined and if they are larger than a threshold difference, will be considered an artifact.

GENERAL DESCRIPTION OF THE PRESENT INVENTION

In this section, a description of the general features of the present invention is given for example by referring to possible embodiments of the invention.

The disclosed method provides, in a first aspect, a medical data processing method for determining the position of an artifact in patient image data describing a set of tomographic slice images of an anatomical structure of a patient. The method comprises executing, on at least one processor of at least one computer, the following exemplary steps which are executed by the at least one processor.

In a (for example first) exemplary step, the patient image data is acquired which describes (for example, defines) the set of tomographic slice images of the anatomical structure (for example, at least part of at least one of the patient's lung or diaphragm), wherein the images are described by color values. More specifically, the color values define the appearance and/or the information content of the image. In one example, the patient image data allows for a differentiation between different parts (for example, different types of tissue) of the anatomical structure. Different types of tissue are characterized by associated different color values. The patient image data may have been generated before the disclosed method is executed by applying a tomographic imaging modality (for example, a computed x-ray modality or a magnetic resonance imaging modality) to the anatomical structure of the patient. Alternatively, generation of the patient image data may be implemented as a step of the disclosed method. Specifically, the patient image data comprises (for example is) 4DCT data.

In one example, the color values are multicolor color values (which are defined for example in the RGB color space). In another example, the color values are greyscale color values. In both cases, the color values are associated with an absorption of the anatomical structure for the imaging radiation used by the tomographic imaging modality. The absorption is one example defined by Hounsfield unit (HU) values of the anatomical structure. In particular, the color values represent HU values of the anatomical structure.

In the following artifacts are considered to be discontinuities in the color values of the images which are not based on the anatomical structure. Artifacts are for example motion artifacts which frequently occur in 4DCT data sets which are due to a vital movement of the patient such as a breathing movement or heartbeat.

In a (for example second) exemplary step, color value difference data is determined for a plurality of pairs of adjacent ones of the slice images. The color value difference data describes (for example, defines) differences in color values for image elements in adjacent slice images by subtracting a color value of an element of a first one of a pair of adjacent slice images from a color value of an element of a second one of the pair of adjacent slice images. Specifically, the subtraction is performed for each one of a plurality of elements of the first one of a pair of adjacent slice images and each one of a plurality of elements of a second one of the pair of adjacent slice images. The color value difference data is determined based on the patient image data and for a plurality of pairs of adjacent ones of the slice images.

In one example, the tomographic slice images are oriented along the craniocaudal axis of the patient. In particular, the pair of adjacent slice images is arranged next to each other along the craniocaudal axis of the patient.

The element of the first one of a pair of adjacent slice images and the element of a second one of the pair of adjacent slice images (whose color values are to be subtracted) may for example each consist of a single pixel or voxel. In particular, the element of the first one of the pair of adjacent slice images and the element of the second one of the pair of adjacent slice images are arranged at corresponding image element positions. Specifically, corresponding image element positions are positions of pixels or voxels of adjacent slice images which correspond to each other (for example, have the same row index and the same column index in the patient image data).

The color value difference data determined for each pair of adjacent slice images may be comprised in a data structure (for example, a multi-dimensional array). In one example the data structure may be a three-dimensional array having entries associated with three indices. The first two indices may be associated with the row and the column of the image element (for example, a pixel or voxel) in the respective slice image. The third index may be associated with a slice number (for example, in a stack of slices arranged along the craniocaudal axis of the patient).

In the following the data structure is called "intermediate layer". The index defining the position of the layer in this data structure is by definition assigned to the index of the subtrahend slice (comprising color values being subtracted). The minuend slice comprises color values from which the color values of the other slice (subtrahend slice) are subtracted (wherein: color value of the minuend slice–color value of the subtrahend slice=color value difference).

In a (for example third) exemplary step, at least one of positive difference data, describing (for example, defining) a subset of the differences and consisting of differences having a positive value (for example, large than zero), or negative difference data, describing (for example, defining) a subset of the differences and consisting of differences having a negative value (for example, smaller than zero) is determined. The at least one of positive difference data or negative difference data is determined based on the color value difference data. In one example, the subset may be a real (for example, strict) subset in the sense that it does not comprise all elements of the color value difference data. In another example all elements of the color value difference data are comprised in the subset of the positive difference data or the subset of the negative difference data.

Accordingly, the third exemplary step may distinguish between (for example, separate) differences having a positive value (for example, larger than zero) and differences having a negative value (for example, smaller than zero) comprised in the color value difference data. This allows for a separate analysis of the positive values and the negative values of the color value difference data (for example by comparing the positive values and/or the negative values separately to reference values).

In a (for example fourth) exemplary step, smoothed difference is determined. The smoothed difference data describes (for example, defines) data describing a smoothing of the differences contained in the at least one of the positive difference data or the negative difference data. The smoothed difference data is determined based on the at least one of the positive difference data or the negative difference data. Determining the smoothed difference data may comprise calculating a running average of the at least one of the positive difference data or the negative difference data. An example for a specific running average used to determine smoothed difference data is provided further down below. The smoothed difference data may be used as reference data. This way a step of acquiring extrinsic reference data may be omitted, and a patient-specific reference can be provided.

In a (for example fifth) exemplary step, artifact position data describing (for example defining) the position of an artifact in the patient image data is determined based on the at least one of the positive difference data or the negative difference data and the smoothed difference data. In one example, determining the artifact position data comprises comparing the at least one of the positive difference data or the negative difference data to the smoothed difference data by establishing a difference between the at least one of the positive difference data or the negative difference data and the smoothed difference data. In one example, establishing a difference between the at least one of the positive difference data or the negative difference data and the smoothed difference data comprises subtracting values of the smoothed difference data from absolute values of at least one of the positive difference data or the negative difference data (for example values of which each is associated with an average of all color value differences determined for one intermediate layer), wherein the respective values on which the subtraction is performed are associated with corresponding intermediate layer positions.

In particular, the method may comprise executing, on the at least one processor of the at least one computer, a step of acquiring difference threshold data describing (for example, defining) a predetermined value of the difference between the at least one of the positive difference data or the negative difference data, and the smoothed difference data. Determining the artifact position data may then comprise comparing the difference between the at least one of the positive difference data or the negative difference data and the smoothed difference data with the predetermined value. This may be accomplished for example by determining whether the difference between the at least one of the positive difference data or the negative difference data and the smoothed difference data is larger than the predetermined value. An artifact is determined to be in the patient image data at a position in the set of tomographic slice images associated with a difference between the at least one of the positive difference data or the negative difference data and the smoothed difference data which is larger than the predetermined value.

In one example, the method further comprises executing, on the at least one processor of the at least one computer, an exemplary step of determining, based on the patient image data, segmented image data describing (for example, defining) a segmentation of the tomographic slice images. The color value difference data may then be determined based on the segmented image data.

Specifically, the segmented image data is determined by applying an image segmentation algorithm to the patient image data. Predefined parts of the patient image data do not serve as a basis for determining the segmented image data (i.e. are excluded from determining the segmented image data), for example are not segmented when determining the segmented image data. This way predefined parts of the patient image data associated with specific elements (for example a patient table or an artificial structure such as an external breathing device) shown on the tomographic slice images may be excluded for determining the color value difference data. Accordingly, a morphological segmentation of the patient image data may be performed.

In one example, the method comprises executing, on the at least one processor of the at least one computer, an exemplary step of acquiring atlas data describing an image-based model of the anatomical structure. The segmentation data may then be determined based on the patient image data and the atlas data, for example by comparing, specifically matching, the atlas data (the image-based model) to the patient image data (the slice images). In particular, the comparing is done for example by applying an image fusion algorithm to the patient image data and the atlas data. This way predefined parts of the patient image date associated with specific elements of the anatomical structure (for example at least part of the heart or at least part of the abdomen of the patient) shown on the tomographic slice images may be excluded for determining the color value difference data.

A binary mask for excluding predefined parts of the patient image data may be established based on segmented image data. Artifacts in 4DCT images may not only be observed in the lung but might be observed for every structure moving during the CT scan, i.e. also for the heart (heartbeat) and the bowels (digestion). However, the user might only be interested in detecting artifacts in the lung. This can be achieved by segmenting the lungs using the atlas data and using the binary mask to define the image elements (for example, pixels or voxels) in the patient image data to be analyzed for artifacts. For example, the atlas data comprises information about the identity (i.e. anatomical classification) of certain parts of the image-based model, and by matching the atlas data to the patient image data, whereby the identity of anatomical structures described by the patient image data corresponding to those described by the atlas data can be determined. Then, only a desired part of the patient image data can be selected as an input for the artifact analysis.

In one example, the patient image data, specifically the segmented patient image data, may be preprocessed by noise filtering, for example by Gaussian smoothing in axial planes, in order to reduce noise. In another example, predefined image elements having a specific color value (for example, a color value associated with a specific HU value) or a specific range of color values (for example, a range of color values associated with a specific range of HU values) may be excluded when determining the color value difference data. Clipping (for example, HU range clipping) of a specific range of color values (for example, a range of color values associated with a specific range of HU values) may be performed. By means of clipping image elements with a (extremely) high color value, which might be caused for example by a metal (of a pacemaker), implant or a bone (for example, rip) may be excluded from the patient image date used to determine the color value difference data.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the at least one processor or is loaded into the at least one memory, or wherein the at least one computer comprises the program storage medium according to the third aspect.

In a fifth aspect, the invention is directed to a system for determining the position of an artifact in the patient image data describing a set of tomographic slice images of an anatomical structure of a patient, the system comprising:
   a) at least one medical imaging device for acquiring the patient image data; and
   b) the at least one computer according to the fourth aspect.

The at least one computer is operably coupled to the at least one medical imaging device for acquiring, from the at least one medical imaging device, the patient image data.

In a sixth aspect, the invention is directed to a system for determining the position of an artifact in the patient image data describing a set of tomographic slice images of an anatomical structure of a patient, the system comprising:
   a) at least one electronic data storage device for storing atlas data describing an image-based model of the anatomical structure;
   b) the at least one computer according to the fourth aspect.

The at least one computer is operably coupled to the at least one electronic data storage device for acquiring, from the at least one electronic data storage device, the atlas data.

Optionally, the system according to the sixth aspect may comprise at least one medical imaging device for acquiring the patient image data, wherein the at least one computer is operably coupled to the at least one medical imaging device for acquiring, from the at least one medical imaging device, the patient image data It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer. An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital light-box. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Atlas data describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data.

The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

DESCRIPTION OF THE FIGURES

In the following, the invention is described with reference to the appended figures which represent a specific embodiment of the invention. The scope of the invention is however not limited to the specific features disclosed in the context of the figures, wherein

FIGS. 6a-6c show the negative signal $s^-$, the positive signal $s^+$, and the combined signal $S^{comb}$ superimposed on the image shown in FIG. 2;

FIG. 1 is a flow diagram illustrating the basic steps of the disclosed method which in the illustrative example of FIG. 1 starts with a step S1 of acquiring patient image data. Then, step S2 is executed which encompasses determining color value difference data. In subsequent step S3 at least one of positive difference data or negative difference data is determined. In step S4 smoothed difference data is determined. The last step shown in FIG. 1 is step S5 which is directed to determining artifact position data.

Figure 1:
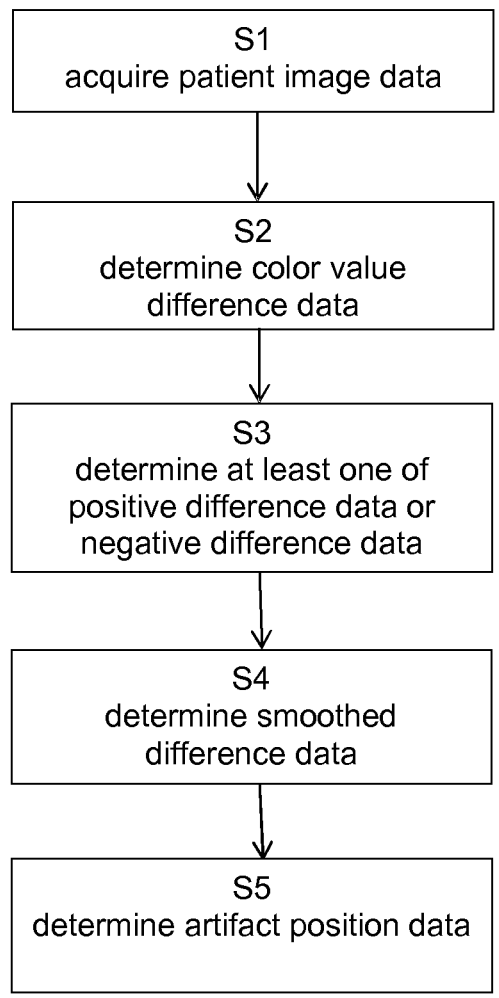
FIG. 1 is a flow diagram showing the basic steps of the disclosed method.

Further down below the disclosed method is explained in detail for one exemplary embodiment. The following symbols are used:

| | |
|---|---|
| $d_{ij}$ | HU value difference for a virtual pixel i in intermediate layer j |
| $\Delta_j$ | $= \min(\|s_{j+1} - s_j\|, \|s_j - s_{j-1}\|)$ minimal signal difference to the next intermediate layers |
| $h_{ik}$ | HU value of pixel i in slice k |
| i | pixel index |
| j, n | intermediate layer index |
| k | slice index |
| $M_j$ | set containing all HU value differences of the intermediate layer j |
| $M_j^+$ | set containing all positive HU value differences of the intermediate layer j |
| $M_j^-$ | set containing all negative HU value differences of the intermediate layer j |
| $N_j^+$ | number of elements in set $M_j^+$ |
| $N_j^-$ | number of elements in set $M_j^-$ |
| $N_j^{pixel}$ | number of pixels in intermediate layer j |
| $N^{ref}$ | defines the number of adjacent intermediate layers in both directions of an intermediate layer considered for computing the reference signal |
| $N^{stack}$ | number of slices which are reconstructed from the same breathing cycle in 4DCT reconstruction |
| $p_j$ | peak significance |
| $r_j$ | reference signal of intermediate layer j |
| $\sigma_j$ | uncertainty of reference signal $r_j$ |
| $\sigma_{reg}$ | minimum uncertainty of reference signal |
| $s^{arti}$ | artifact signal |
| $s^{bg}$ | background signal |
| $s_j^+$ | positive signal |
| $s_j^-$ | negative signal |
| $s_j^{comb}$ | combined signal |
| $T_{breath}$ | breathing period |
| $v_{table}$ | table velocity |
| w | slice thickness |
| $z_j$ | axial position of intermediate layer j |
| $\zeta_k$ | axial position of slice k |

The patient image data describing a set of tomographic slices comprises in this example a stack of axial slices along the cranio-caudal (axial) direction, where a slice k is located at the axial position $\zeta_k$. Moreover, (virtual) intermediate layers which are located in between these axial slices (per definition) are defined, i.e. an intermediate layer j is located at $$z_j = \frac{\zeta_{k+1} + \zeta_k}{2},$$

where k=j.

The computation of the artifact signal (representing the color value difference data) is based on HU value differences along the craniocaudal direction. The HU value difference for a (virtual) pixel i in an intermediate layer j is computed by $$d_{ij} = h_{ik+1} - h_{ik},$$

where $h_{ik}$ is the HU value of pixel i of slice k and k=j.

To differ between positive and negative signals (wherein a positive signal represents the positive difference data and a negative signal represents the negative difference data), a set containing all HU value differences of an intermediate layer j is defined:

$$M_j = \{d_{ij}, \text{ with } i=1, \ldots, N_j^{pixel}\},$$

where $N_j^{pixel}$ is the number of pixels of that intermediate layer.

The according sets for the positive and negative signals are then defined as:

$$M_j^+ = \{m \in M_j : m > 0\}$$

$$M_j^- = \{m \in M_j : m > 0\}.$$

Taking the average of all absolute values in these sets give the positive and the negative signals for an axial position $z_j$:

$$s_j^+ = \frac{1}{N_j^+} \sum_{i=1}^{N_j^+} |m_{ij}^+|, m_{ij}^+ \in M_j^+$$

$$s_j^- = \frac{1}{N_j^-} \sum_{i=1}^{N_j^-} |m_{ij}^-|, m_{ij}^- \in M_j^-,$$

where $N_j^+(N_j^-)$ is the number of elements in set $M_j^+(M_j^-)$.

For comparison the combined signal is computed by $$s_j^{comb} = \frac{s_j^+ + s_j^-}{2}.$$

Both artifact signals, s⁺ and s⁻, are analyzed in the same manner. Therefore, the superscript (+/−) is omitted in the following. Accordingly, the analysis presented here for an artifact signal s is applied for both positive and negative artifact signals (i.e. for the positive difference data and the negative difference data).

The analysis of the artifact signal is summarized as follows. First a reference signal with its uncertainty is computed. Second, local maxima (peaks) are detected in the artifact signal. Significant peaks are expected to be caused by artifacts and called "artifact peaks" here. The positions of these artifact peaks are the detected artifact positions. To check the peak significance, the artifact signal is compared against the reference signal. If the deviation exceeds a threshold value, the peak is considered to be significant.

Specifically, the reference signal $r_j$ of an intermediate layer j (representing the smoothed difference data) is computed by taking a 4DCT specific running average of the signal s $$r_j = \frac{1}{2N^{ref}} \sum_{\substack{n=j-N^{ref} \\ n \neq j}}^{j+N^{ref}} s_n,$$

where the summation is done over intermediate layers n and $N^{ref}$ defines the number of considered intermediate layers in both directions from the intermediate layer j. In one example, the parameter $N^{ref}$ is chosen large enough, in order to get a representative reference signal. Furthermore, $N^{ref}$ is chosen small enough that no additional artifact peak is included in the range $[j-N^{ref}, j+N^{ref}]$ for an artifact peak at intermediate layer j.

In 4DCT reconstruction a stack of slices is reconstructed from the same breathing cycle and artifacts occur between these stacks due to breathing irregularities. The number of slices within a stack depends on the scanner parameters and the patient's breathing frequency:

$$N^{stack} = \frac{v_{table} T_{breath}}{w},$$

where $v_{table}$ is the table velocity, $T_{breath}$ is the breathing period, and w is the slice thickness (for example, 2 to 3 mm). In one example, $N^{ref}$ is not chosen larger than $N^{stack}$:

$$N^{ref} \leq N^{stack},$$

to ensure that reference signal for an artifact peak is not computed from a signal of another artifact peak.

The uncertainty $\sigma_j$ of the reference signal $r_j$ is estimated by taking the standard deviation over all signals used in computing the reference signal plus adding fixed contribution $\sigma_{reg}$:

$$\sigma_j = \sqrt{\frac{1}{2N^{ref}-1} \sum_{\substack{n=j-N^{ref} \\ n \neq j}}^{j+N^{ref}} (s_n - r_j)^2 + \sigma_{reg}^2}.$$

The parameter $\sigma_{reg}$ is introduced to account for the fact that the standard deviation might underestimate the true uncertainty of the reference signal due to the limited number of considered data points.

A peak is considered to be significant, when the peak significance $$p_j = \frac{s_j - r_j}{\sigma_j}$$

exceeds a threshold:

$$p_j > 2.$$

Artifact peaks are characteristic peaks as they are only formed by a single data point. Peaks which are only formed by a single data point are called singular peaks here. To check whether a peak is singular, the distance of the signal $s_j$ to the closest signal of the upper and lower intermediate layer is computed as $$\Delta_j = \min(|s_{j+1} - s_j|, |s_j - s_{j-1}|).$$

A peak is considered to be singular, when this distance is significant, i.e.

$$\frac{\Delta_j}{\sigma_j} > 2.$$

In summary, for an intermediate layer j an artifact is detected, when the following condition is fulfilled:

$$\min\left(p_j, \frac{\Delta_j}{\sigma_j}\right) > 2.$$

The artifact position (comprised in the artifact position data) is specified to be the position of the intermediate layer j.

In one example, the analysis is performed separately for both the positive and the negative signal. The finally detected artifacts are the union of the detected artifacts in the positive and negative signal.

Figure 2:
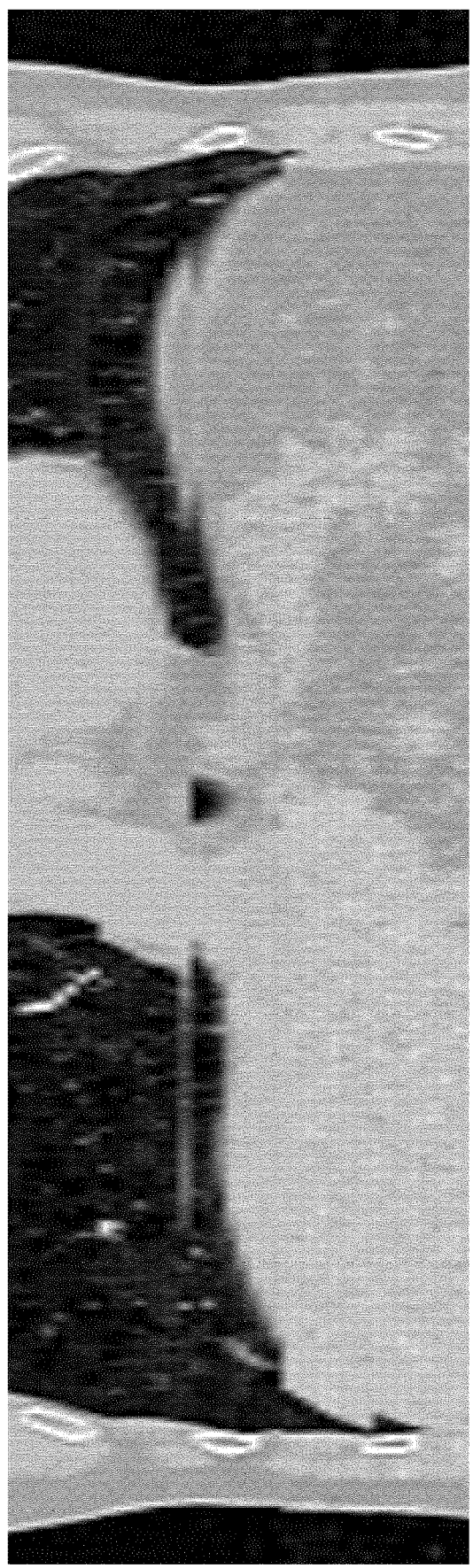
FIG. 2 depicts a coronal view of a 4DCT data set showing some typical artifacts.

FIG. 2 depicts the coronal view of a 4DCT dataset showing some typical artifacts for example along the upper edge of the diaphragm. For better visualization a linear image interpolation is done. The 4DCT dataset of FIG. 2 shows four artifacts, which manifest as discontinuities in the anatomy depicted by the image.

Figure 3:
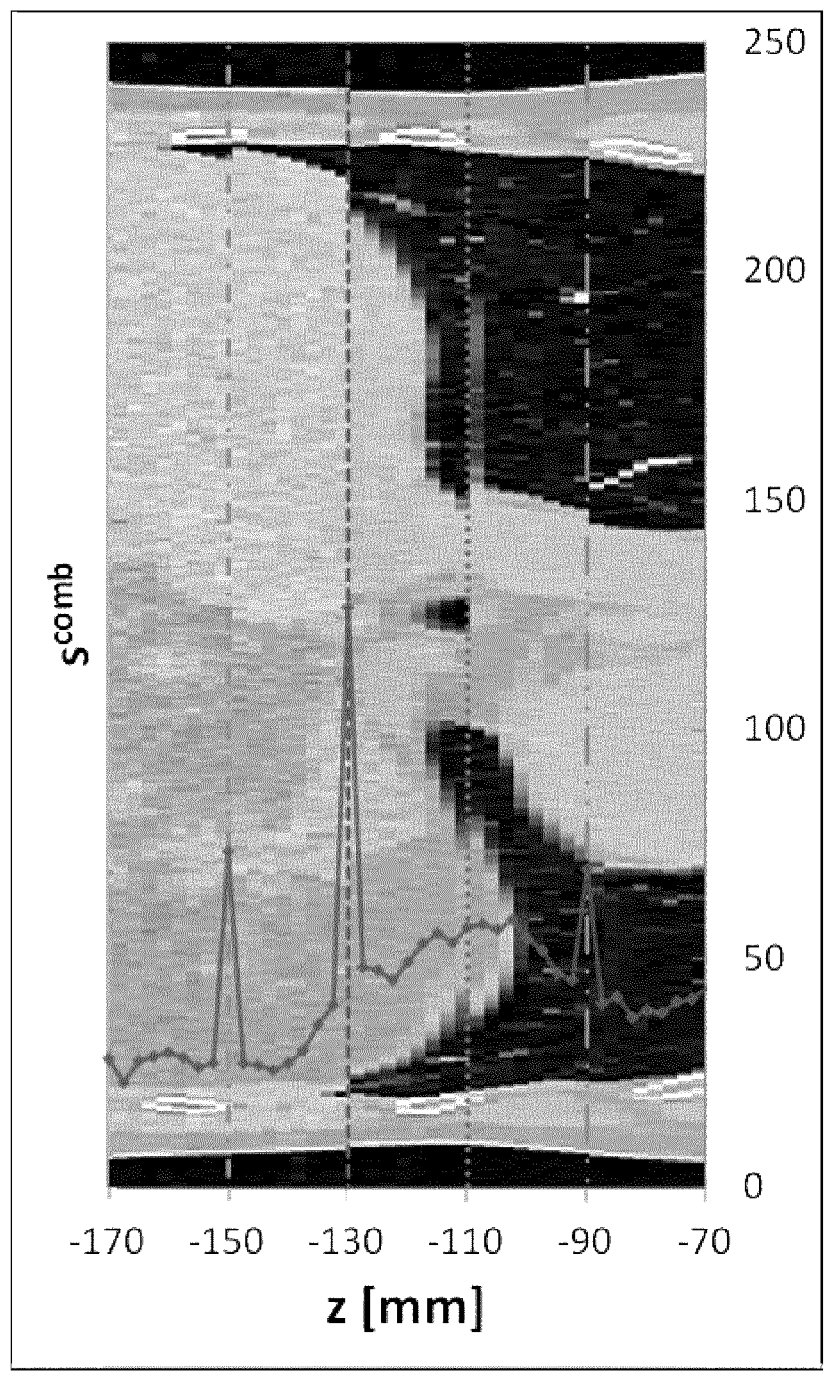
FIG. 3 shows a combined signal $S^{comb}$ superimposed on the 4DCT data set shown in FIG. 2.

FIG. 3 shows a combined signal $s^{comb}$ superimposed on the 4DCT data set shown in FIG. 2 (the background image is the rotated image shown in FIG. 2 without image interpolation). The combined signal $s^{comb}$ is computed by taking the mean squared HU value difference.

The vertical lines in FIG. 3 represent artifact locations. As shown by FIG. 3, only three out of four artifacts may be detected by the combined signal $s^{comb}$. The artifact located at the vertical dotted line is not represented by the combined signal $s^{comb}$. There is not even a small peak found in the signal at the position at the vertical dotted line.

FIG. 3 shows that the approach based on computing simply HU value differences to obtain the combined signal $s^{comb}$ suffers from low sensitivity. Some type of artifacts are not detected with the approach based on simply computing HU value differences, even though may be easily identified visually (see FIGS. 2 and 3).

The reason why the approach based on computing simply HU value differences to obtain the combined signal $s^{comb}$ is that the computed signal $s^{comb}$ does not only contain the artifact signal $s^{art}$ but also a background signal $s^{bg}$ which is mainly caused by the changing anatomy along the cranio-caudal direction (plus CT noise):

$$s^{comb} = s^{bg} + s^{art}$$

Some type of artifacts lead simultaneously to a dip in the background signal $s^{bg}$ and to a peak in the artifact signal $s^{art}$. Therefore, the peak in the combined signal $s^{comb}$ becomes less distinct and might not be distinguished from the background signal variations. In the worst case scenario, no peak is observed at all in the combined signal $s^{comb}$ and there is no chance to detect the artifact (as seen in FIG. 3).

Figure 4:
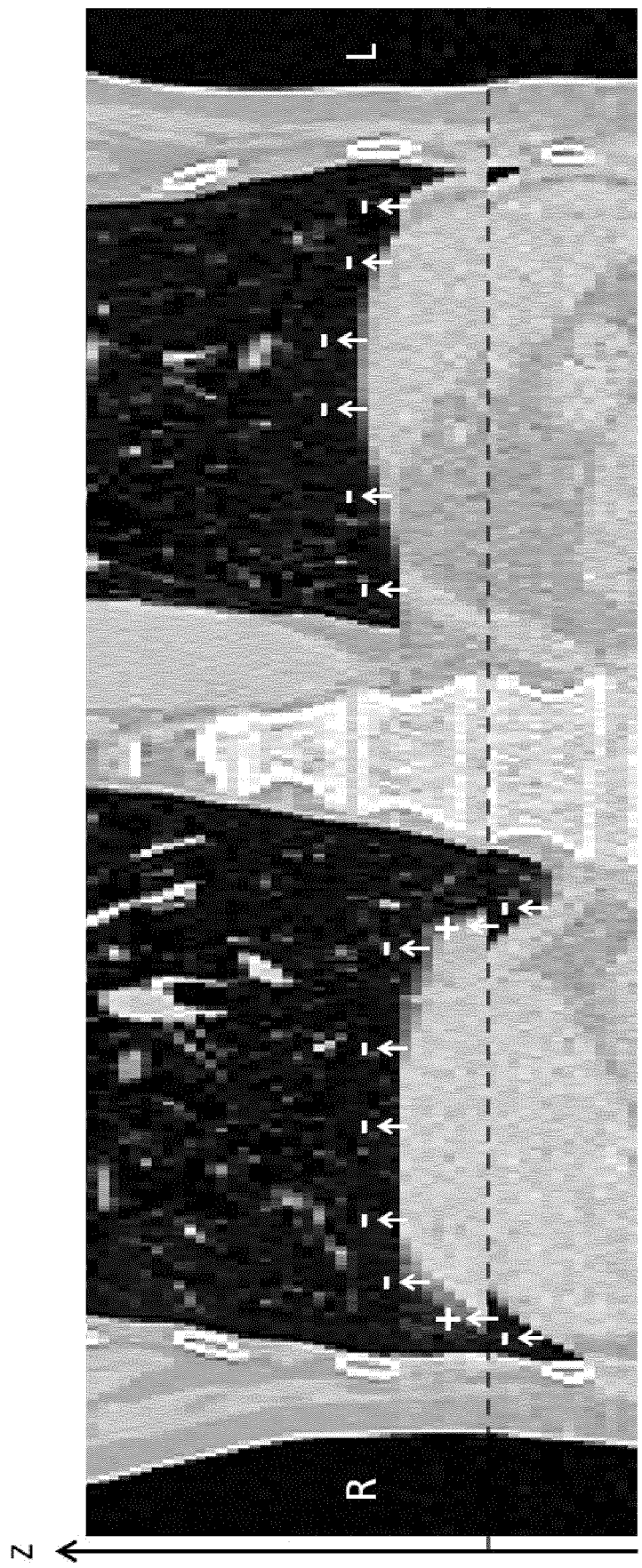
FIG. 4 shows a coronal view of a 4DCT data set with overlapping and incomplete artifacts.

An example of such a situation is a typical overlapping artifact as shown in FIG. 4. The HU value differences are computed along the z-axis as indicated by the small white arrows in FIG. 4. the sign of the differences are represented by either a "+" or a "−" sign at the tip of each arrow in FIG. 4. The dashed line in FIG. 4 indicates the location of the overlapping artifact, which is clearly visible in the right lung. In FIG. 4 the background signal $s^{bg}$ in the region around the artifact is dominated by the diaphragm.

Figure 5B:
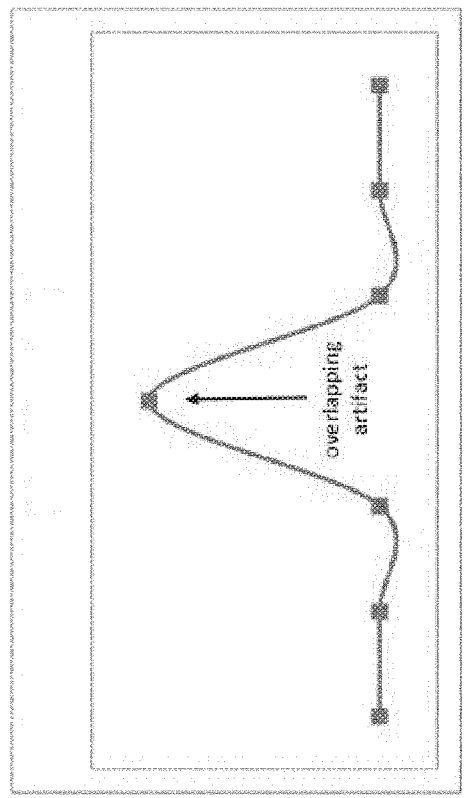
FIGS. 5a-5c are is a schematic illustration of negative (a), positive (b), and combined (c) signals determined based on HU value differences in vicinity to an overlapping artifact.
Figure 5A:
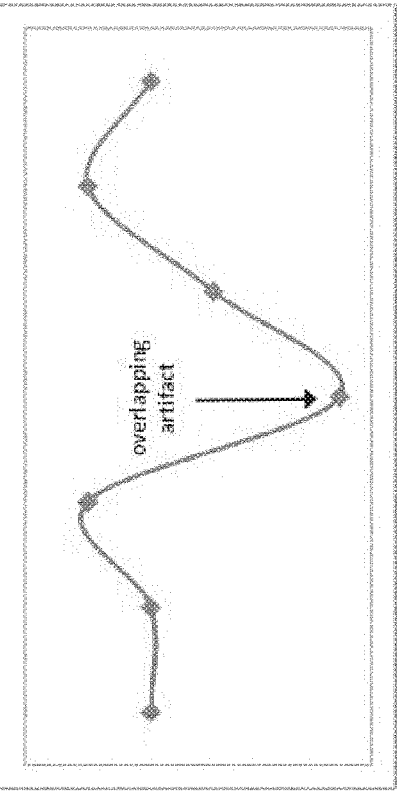
Figure 5C:
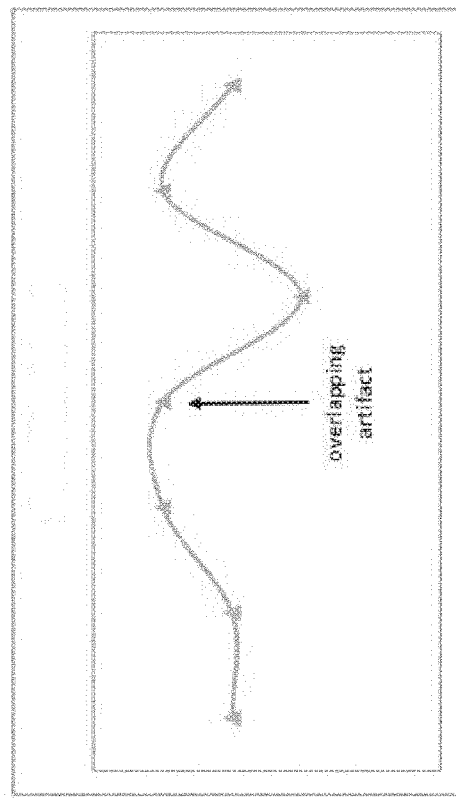

FIGS. 5a-5c are a schematic illustration of negative (see FIG. 5(a)), positive (see FIG. 5(b)), and combined (see FIG. 5(c)) signals determined based on HU value differences in vicinity to an overlapping artifact. As shown by FIG. 5, the artifact causes a dip in the negative signal (see FIG. 5(a)) and a peak in the positive signal (see FIG. 5(b)). In the combined signal (see FIG. 5(c)), the information about the artifact is lost.

This is exactly the reason why the simple HU value difference approach to obtain the combined signal $s^{comb}$ is not able to detect the overlapping artifact in FIG. 3. However, splitting the combined signal $s^{comb}$ into two signals, $s^+$ ("positive signal") and $s^-$ ("negative signal"), allows for separating the background and artifact signal for duplicated and overlapping diaphragm artifacts. The positive (negative) signal is the signal obtained by only considering positive (negative) HU value differences in the computation of the signal.

In FIGS. 5a and 5b, the background signal caused by the diaphragm is visible in the negative signal (FIG. 5a) but not in the positive signal (FIG. 5b). On the contrary, the artifact signal is visible in the positive signal (FIG. 5b) but not in the negative signal (FIG. 5a). Therefore, an artifact peak is visible in the positive signal (FIG. 5a), even it is not visible in the combined signal (see FIG. 5c).

FIGS. 6a-6c show the negative signal $s^-$(FIG. 6a), the positive signal $s^+$(FIG. 6a), and the combined signal $s^{comb}$ (FIG. 6a) superimposed on the image shown in FIG. 2. FIG. 6a-6c illustrate how the separation into a positive and negative signal helps to detect the artifact that was missed in the combined signal shown in FIG. 3. As shown by FIG. 6c, the artifact located at the vertical dotted line is not detected in the combined signal $s^{comb}$. However, it is detected in the positive signal $s^+$.

Peaks caused by artifacts (also called "artifact peaks" here) are in general different from local maxima caused by changing anatomy along the head-feet direction, see FIG. 6a-6c for example. If the slices in the 4DCT data sets are reconstructed without any overlaps, the peak is expected to be represented by exactly one image element (for example, pixel or voxel). If overlapping slices are reconstructed, two slices share partly the same information; therefore, the peak might be represented by one or two image elements data points (for example, pixel or voxel). This information may be used for a peak-detection algorithm customized for 4DCT artifacts detection (i.e. for determining the artifact position data).

Figures 7A, 7B:
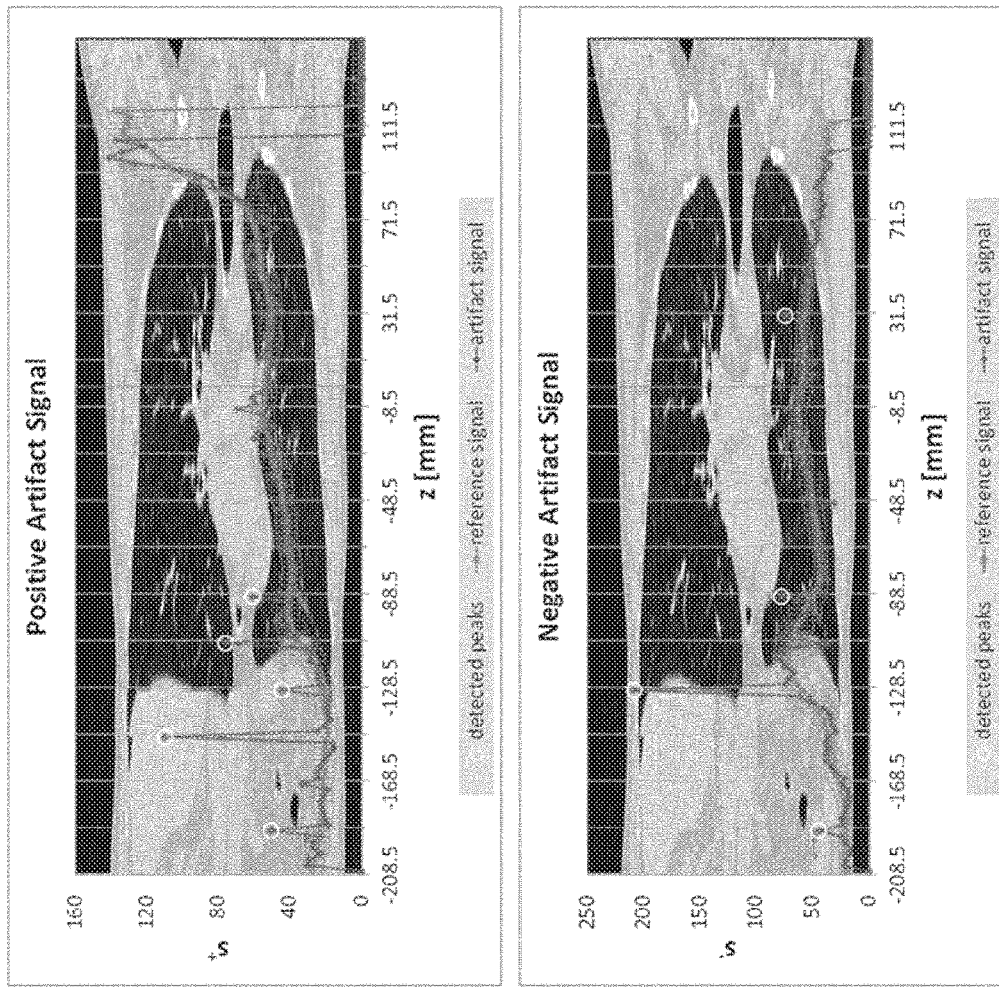
FIGS. 7a and 7b show the negative signal $s^-$ and the positive signal $s^+$ superimposed on another 4DCT data set.
Figure 8C:
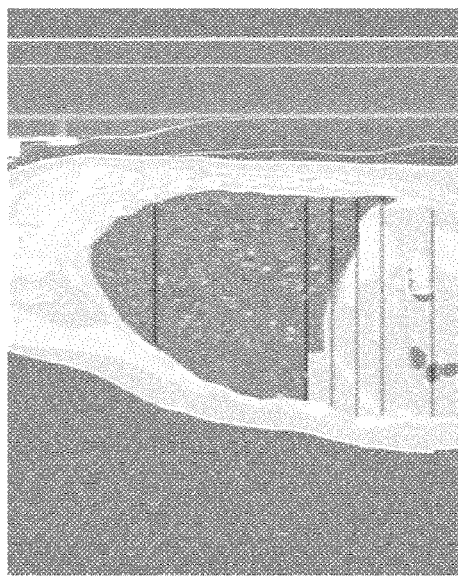
FIGS. 8a-8c are summaries of the detected artifacts presented in FIG. 7.
Figure 8B:
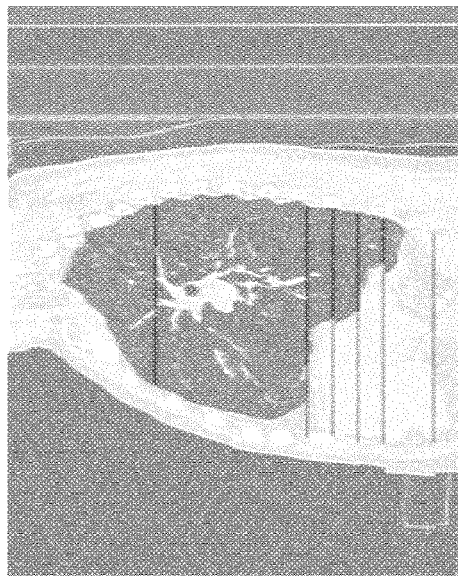
Figure 8A:
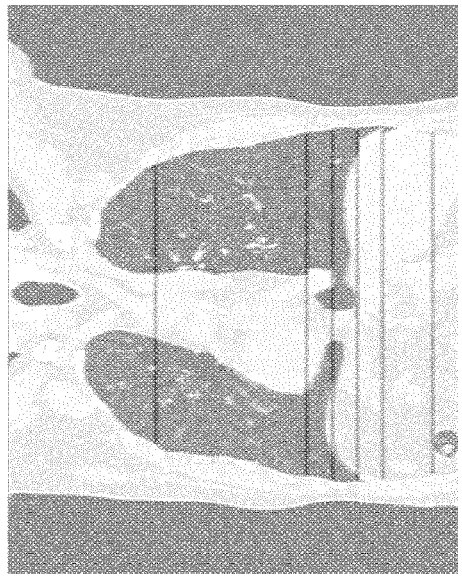

The feasibility of the disclosed method was tested for another 4DCT data set shown in FIGS. 7a-7b. FIGS. 7a and 7b show the negative signal $s^-$ (FIG. 7b) and the positive signal $s^+$ (FIG.7a) superimposed on the 4DCT data set. FIGS. 8a-8c are summaries of the detected artifacts presented in FIGS. 7a and 7b.

The 4DCT data set shown in FIGS. 7a and 7b is acquired with a GE Discovery CT590 RT CT scanner in cine mode. Therefore, the artifacts can only occur between certain slices, where the couch position has changed. At a given couch position, a region of 20 mm is scanned simultaneously corresponding to the $z^-$ coverage of the detector. This is also the minimum distance of two artifact. The artifacts detected by means of the disclosed method correspond to the artifacts found by visual inspection. Furthermore, the positions artifacts are compatible with the positions where the couch position has changed.

Figure 9A:
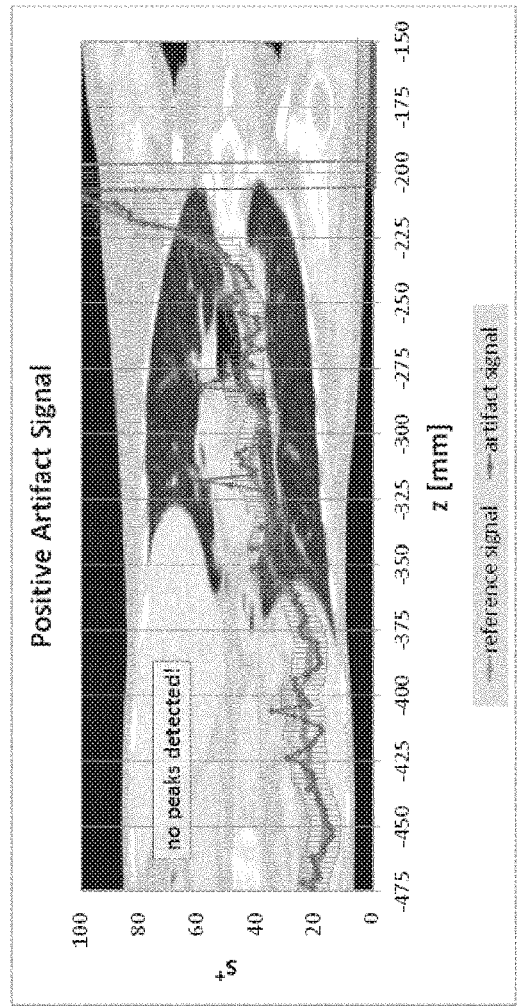
FIGS. 9a and 9b show the negative signal s⁻ and the positive signal s⁺ for a nearly perfect 4DCT image without any artifacts.
Figure 9B:
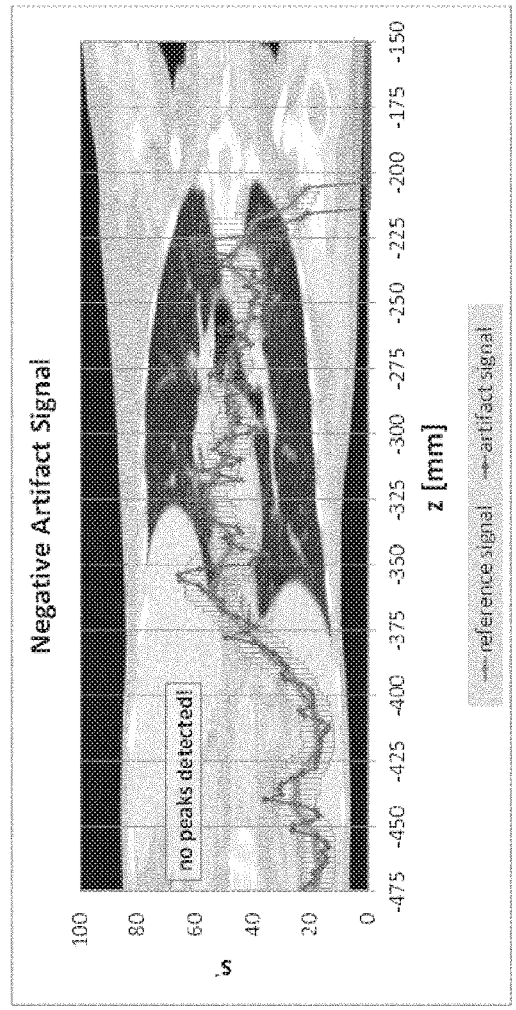

In FIGS. 9a and 9b the disclosed method was applied to a nearly perfect 4DCT data set without any artifacts. Neither the negative signal $s^-$ nor the positive signal $s^+$ provides an indication for an artifact.

Figure 10:
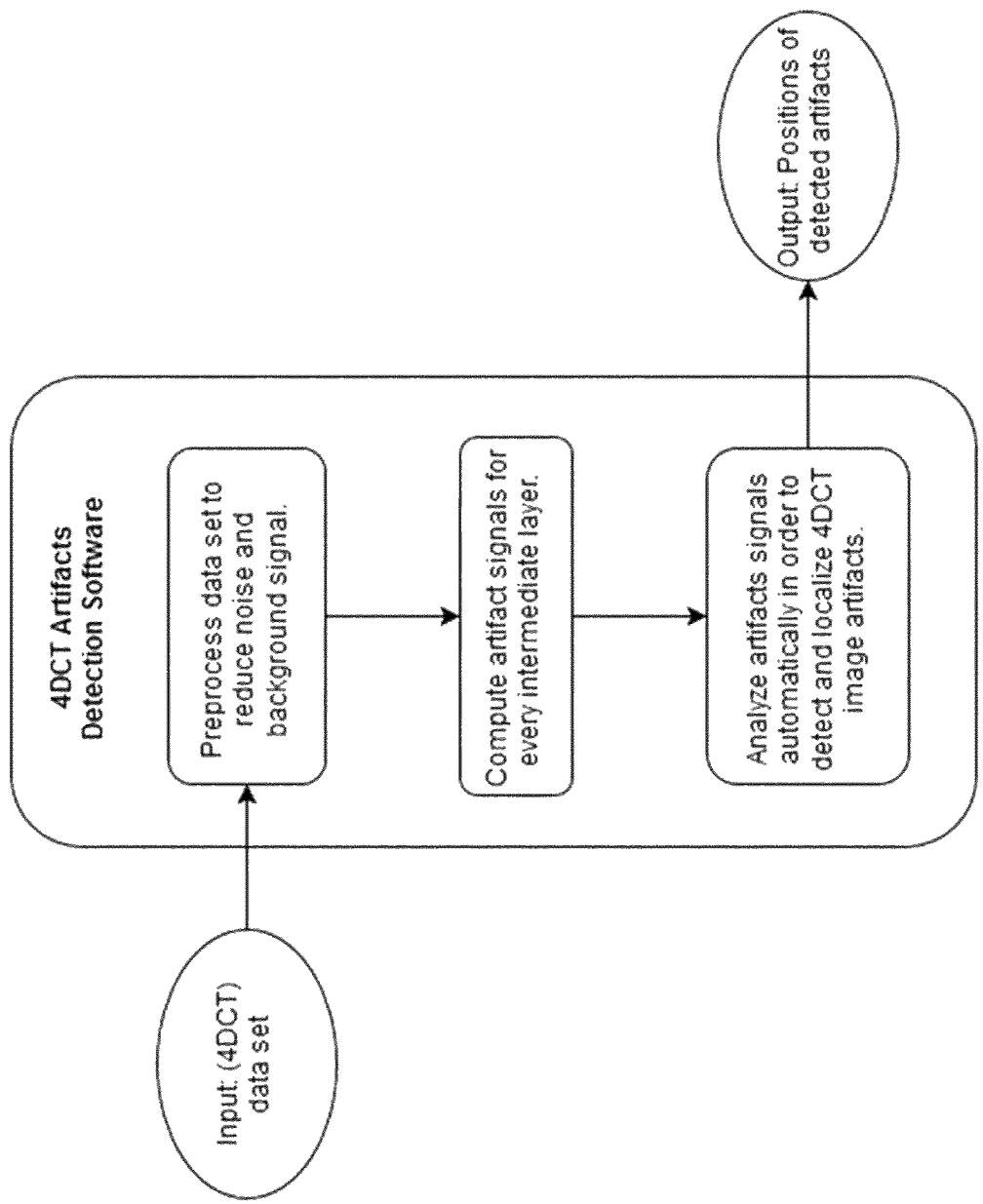
FIG. 10 shows a workflow for determining the position of an artifact.

FIG. 10 shows an overview of an exemplary workflow for determining the position of an artifact. First a (4DCT) data set is inputted. The data set is preprocessed to reduce noise and background signal. Subsequently artifact signals are computed for every intermediate layer. The artifact signals are then analyzed automatically, in order to detect and localize (4DCT) image artifacts. Finally, the positions of the detected artifact are outputted.

Figure 11:
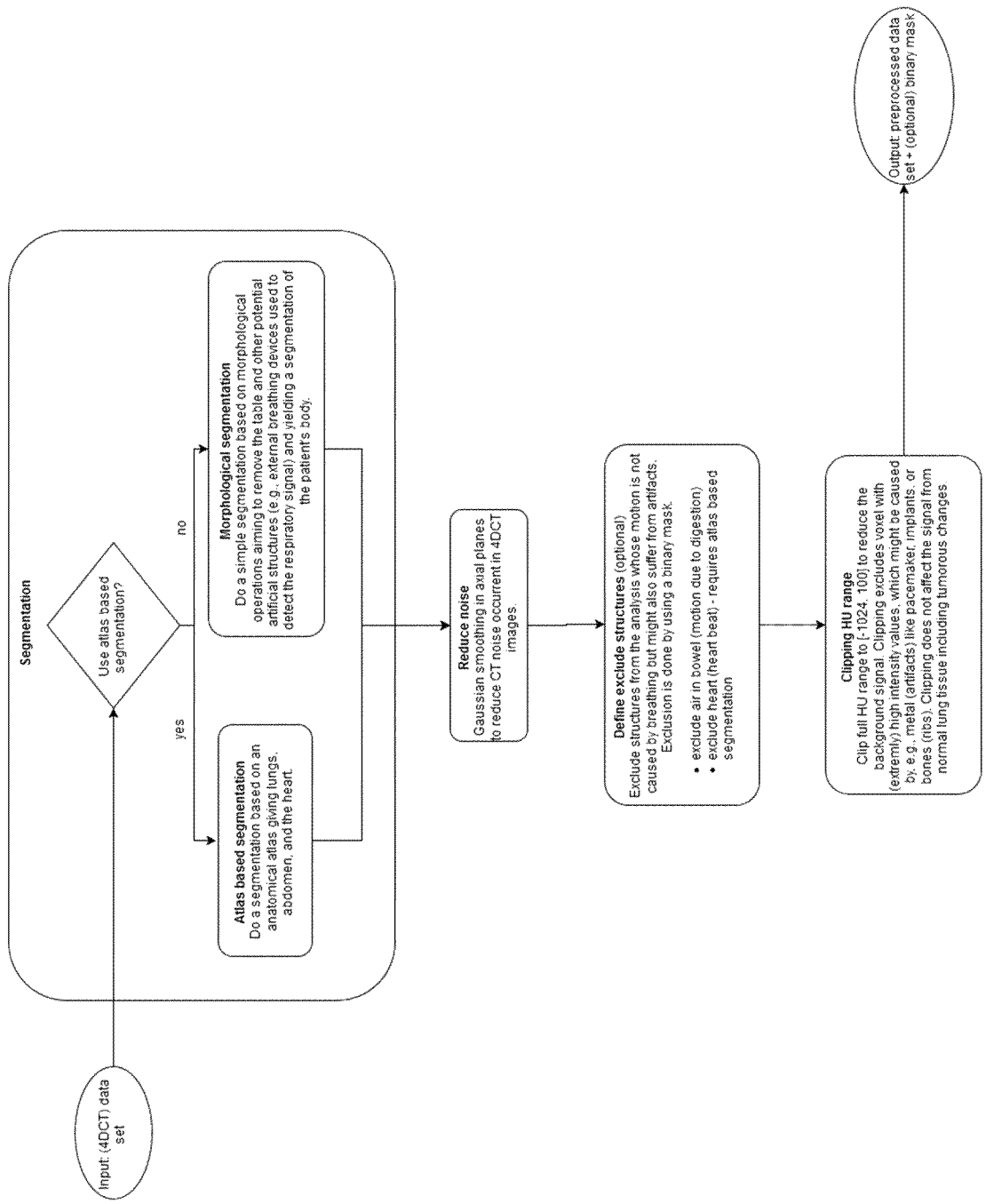
FIG. 11 shows a workflow for preprocessing of CT data sets.

In FIG. 11 an exemplary workflow for preprocessing a (4DCT) data set is depicted. After inputting the (4DCT) data set it is decided whether an atlas based segmentation shall be performed. If yes, an atlas based segmentation based on an anatomical atlas giving for example lungs, abdomen, and the heart performed. If no, a morphological segmentation based on morphological operations aiming to remove for example the patient table and other artificial structures (e.g. external breathing devices to detect the respiratory signal) and yielding a segmentation of the patient's body is done. Subsequently, Gaussian smoothing in axial planes to reduce CT noise occurring in 4DCT images is performed. Optionally, structures whose motion is not caused by breathing but might also suffer from artifacts are excluded from the analysis. The exclusion may be done using a binary mask. For example the air in the bowel may be excluded (motion due to digestion). In another example, the heart (heart beat) may be excluded (this may require an atlas based segmentation). Afterwards, the HU range is clipped. For example, the full HU range may be clipped to [−1024, 100] to reduce the background signal. By clipping image elements (pixels or voxels) with (extremely) high intensity values, which might be caused for example by metal (artifacts) from pacemaker, implants, or bones (ribs), may be excluded. In particular, clipping does not affect the signal from normal lung tissue including tumorous changes. Finally, a preprocessed data set and optionally a binary mask is outputted.

Figure 12:
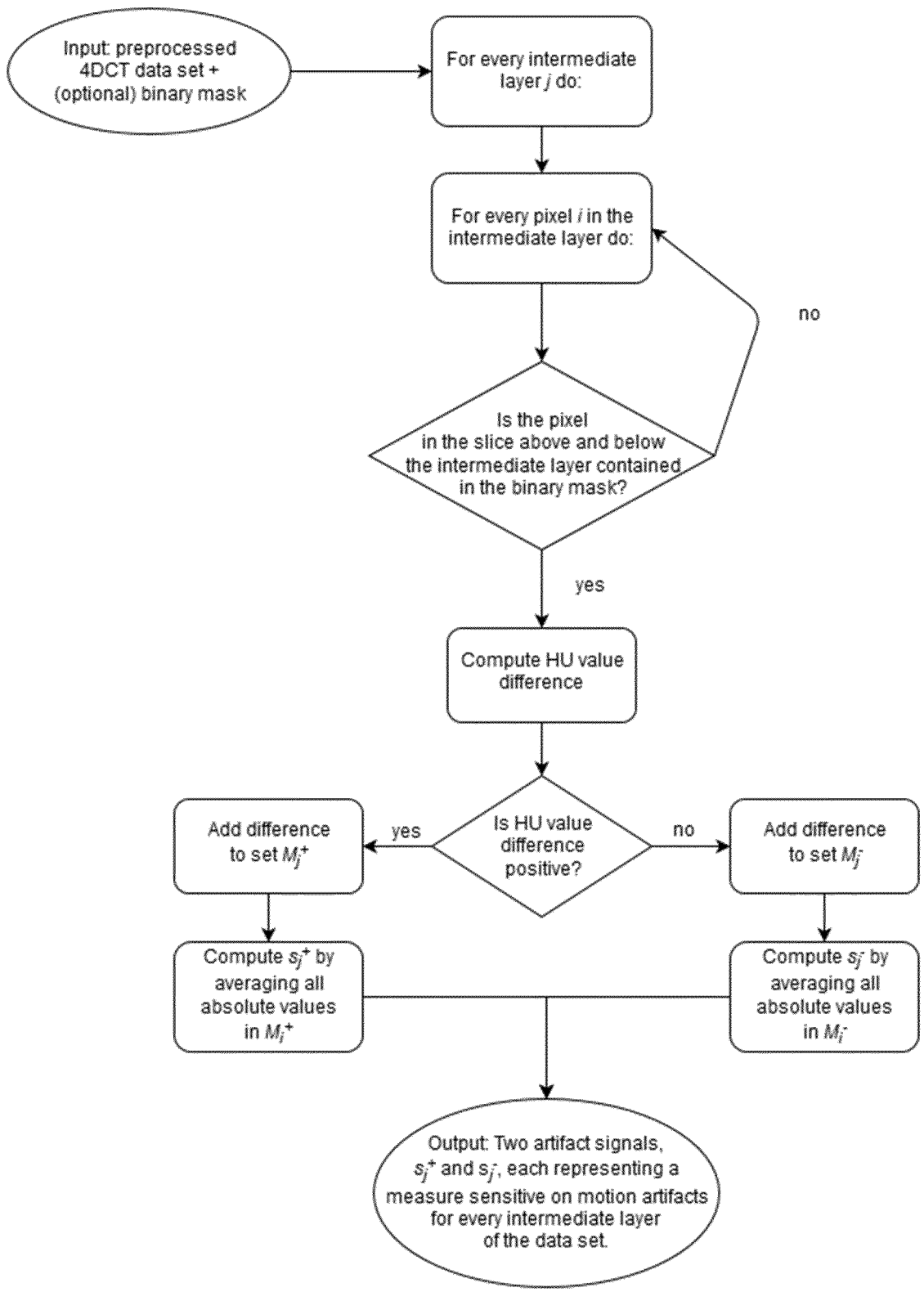
FIG. 12 shows a workflow for computing artifact signals from an CT data set.

FIG. 12 shows an exemplary workflow for computing artifact signals from an 4DCT data set. First a preprocessed 4DCT data set and optionally a binary mask is inputted. A loop for every intermediate layer j and a loop for every pixel i in the intermediate layer is established, in order to decide whether the pixel in the slice above and below the intermediate layer is contained in the binary mask. If yes, an HU value difference is computed. If the HU value difference is positive, the difference is added to the set $M_j^+$. If the HU value difference is negative, the difference is added to the set $M_j^-$. A positive signal $s_j^+$ is computed by averaging all absolute values in $M_j^+$. A negative signal $s_j^-$ is computed by averaging all absolute values in $M_j^-$. Finally, two artifact signals, $s_j^+$ and $s_j^-$, each representing a measure sensitive on motion artifacts for every intermediate layer of the data set, are outputted.

Figure 13:
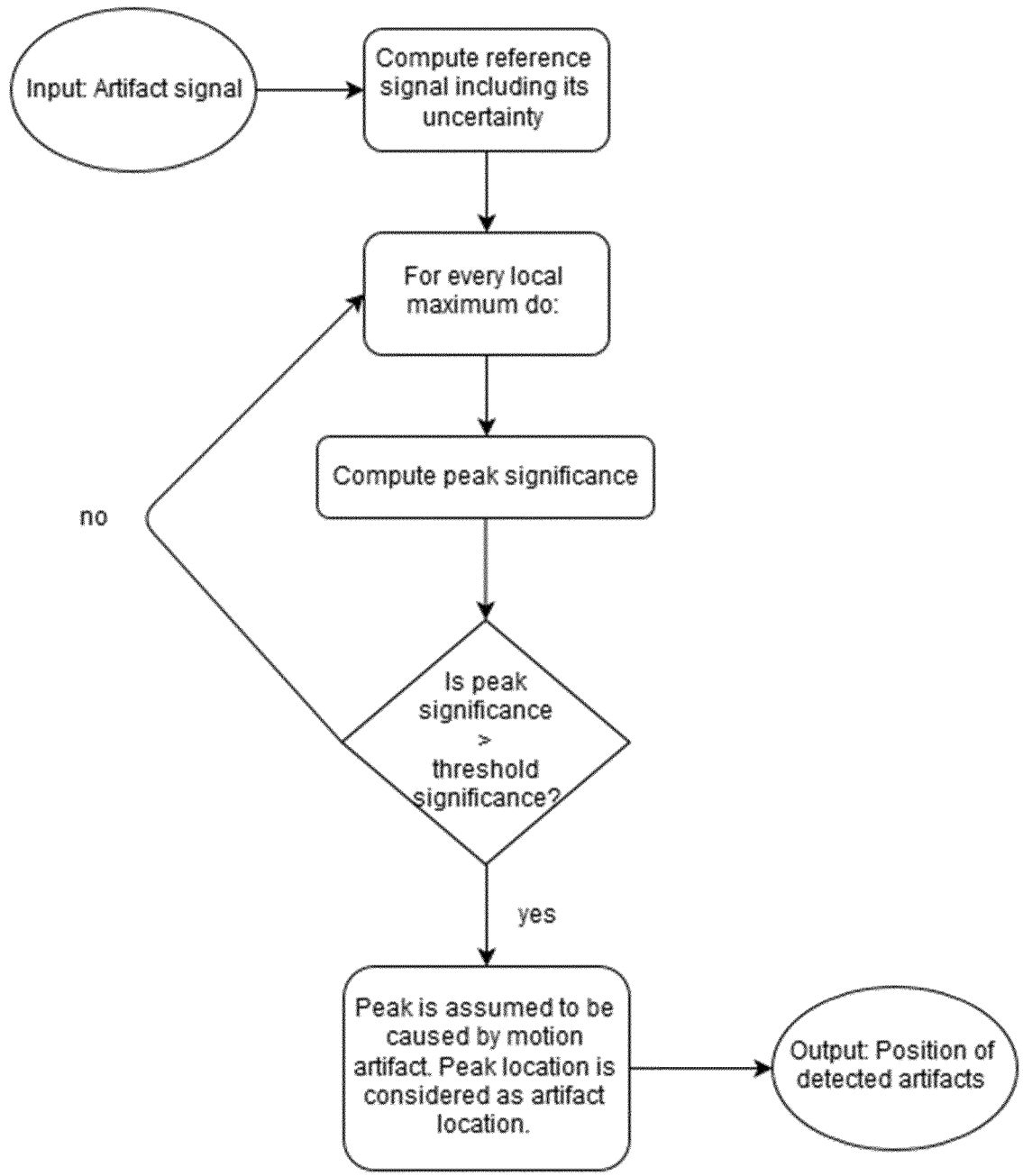
FIG. 13 shows a workflow for analyzing artifact signals and determining the position of the artifacts.

In FIG. 13 an exemplary workflow for analyzing an artifact signal, for example $s_j^+$ or $s_j^-$ is shown. First an artifact signal is inputted, for example $s_j^+$ or $s_j^-$. Subsequently a reference signal including its uncertainty is computed. For every local maximum a peak significance is computed. A loop is established, in order to decide whether the peak significance is larger than a threshold significance. If yes, the peak is assumed to be caused by an artifact, for example a motion artifact. The peak position is considered as the artifact location. Finally, the positions of detected artifacts are outputted.

Figure 14:
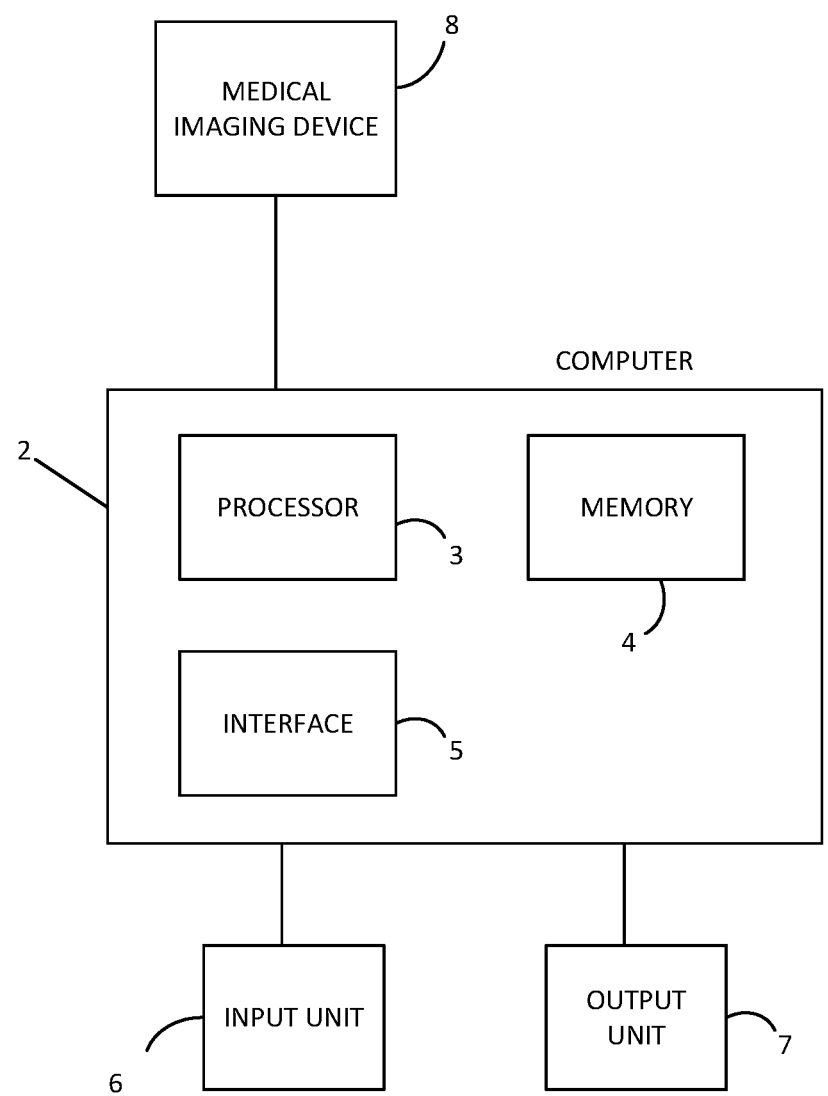
FIG. 14 shows a system performing the disclosed method.

FIG. 14 shows an exemplary system for performing the disclosed method. The system comprises a computer 2 as well as a medical imaging device 8 operably coupled to the computer 2. The computer 2 comprises a processor 3, a memory 4 and an interface 5. The computer 2 is connected to an input unit 6, such as a mouse, a keyboard or a touch-sensitive surface, and an output unit 7 such as a display, a speaker or a tactile sensation generation unit. A program causing the computer 2 to perform the disclosed method may be loaded into the memory 4 of the computer. In one embodiment the program may be stored on a program storage medium comprised in or connected to the computer 2. Furthermore, the computer 2 may be operably coupled to at least one electronic data storage device for storing atlas data.

The disclosed method is applicable for analyzing motion artifacts in 4DCT data sets. However, it is not limited to 4DCT data sets as it generally applicable for analyzing motion artifacts in CT data sets. Therefore, the disclosed method is also applicable for detecting artifacts in MIPs (maximum-intensity projection images generated from 4DCTs), planning CTs . . . .

Advantages of the disclosed method are:
no elastic registration necessary (only optionally when atlas based segmentation is used)
can be applied to every dataset of a 4DCT
does not require a minimum number of data sets
does not require an artifact-free data set
applicable to MIPs, which are often used in the clinics
independent on how the 4DCT/data set was acquired, i.e. can be applied for both helical and cine 4DCTs
no breathing signal required
useful in research, where breathing signal is most often not available for the 4DCTs
useful for product development, as additional uploads and communication issues are avoided
accurate localization of the artifacts
patient-specific approach.

The invention claimed is:

1. A method for determining the position of an artifact in patient image data, the method comprising:
acquiring patient data at an input of a medical data processing system comprising a memory device, a processor, and the input, the patient image data describing a set of tomographic slice images of an anatomical structure of an associated patient, wherein the tomographic slice images of the patient image data are described by color values;
determining by the processor of the medical data processing system, based on the patient image data and for each of a plurality of pairs of adjacent ones of the tomographic slice images, a corresponding plurality of color value difference data sets describing differences in color values of image elements between the adjacent ones of the tomographic slice images, each selected color value difference data set being determined as differences by subtracting, for a corresponding selected pair of adjacent tomographic slice images, a color value of an element of a first one of the selected pair of adjacent tomographic slice images from a color value of an element of a second one of the selected pair of adjacent tomographic slice images;
determining by the processor of the medical data processing system for the plurality of color value difference data sets:
at least one of a corresponding plurality of positive difference data sets or a corresponding plurality of negative difference data sets, a selected positive difference data set relative to a corresponding selected color value difference data set describing a subset of the differences resulting from the subtracting of the color value of the element of the first one of the pair of adjacent tomographic slice images corresponding to the selected color value difference data set from the color value of the element of the second one of the selected pair of adjacent tomographic slice images corresponding to the selected color value difference data set and consisting of only differences having a positive value, and a selected negative difference data set relative to the corresponding selected color value difference data set describing a subset of the differences resulting from the subtracting of the color value of the element of the first one of the pair of adjacent tomographic slice images corresponding to the selected color value difference data set from the color value of the element of the second one of the selected pair of adjacent tomographic slice images corresponding to the selected color value difference data set and consisting of only differences having a negative value;
determining by the processor of the medical data processing system, based on the at least one of the plurality of positive difference data sets or the plurality of negative difference data sets, smoothed difference data describing a smoothing of the differences contained in the at least one of the plurality of positive difference data sets or the plurality of negative difference data sets; and
determining the artifact position data by the processor of the medical data processing system by comparing the smoothed difference data with the at least one of the plurality of positive difference data sets or the plurality of negative difference data sets and determining a difference between the smoothed difference data and the at least one of the plurality of positive difference data sets or the plurality of negative difference data sets in accordance with the comparing, the artifact position data describing the position of the artifact in the patient image data using separately the plurality of positive difference data sets or the plurality of negative difference data sets in accordance with the determining of the plurality of positive difference data sets or the plurality of negative difference data sets.

2. The method according to claim 1, comprising:
acquiring difference threshold data at the input of the medical processing system, the difference threshold data describing a predetermined value of the difference determined between the at least one of the plurality of positive difference data sets or the plurality of negative difference data sets and the smoothed difference data,
wherein the artifact is determined to be in the patient image data at a position in a set of tomographic slice images associated with a difference between the at least one of the plurality of positive difference data sets or the plurality of negative difference data sets and the smoothed difference data which is larger than the predetermined value.

3. The method according to claim 1, wherein the determining the smoothed difference data comprises:
calculating by the processor of the medical data processing system a running average of the at least one of the plurality of positive difference data sets or the plurality of negative difference data sets.

4. The method according to claim 1, further comprising:
determining, by the processor of the medical data processing system based on the patient image data, segmented image data describing a segmentation of the set of tomographic slice images,
wherein the color value difference data is determined based on the segmented image data.

5. The method according to claim 1, wherein the element of the first one of the selected pair of adjacent tomographic slice images and the element of the second one of the selected pair of adjacent tomographic slice images are arranged at corresponding image element positions.

6. The method according to claim 1, wherein the element of the first one of the selected pair of adjacent tomographic slice images and the element of the second one of the selected pair of adjacent tomographic slice images each comprise a single pixel or voxel.

7. The method according to claim 1, further comprising: associating the color values with Housefield unit values of the anatomical structure.

8. The method according to claim 1, wherein the acquiring the patient image data comprises acquiring patient image data describing a set of tomographic slice images of the anatomical structure of the associated patient that are oriented along the craniocaudal axis of the patient.

9. The method according to claim 4, further comprising determining the segmented image data by applying an image segmentation algorithm to predefined parts of the patient image data to an exclusion of other predefined parts of the patient image data whereby the other predefined parts of the patient image data do not serve as a basis for determining the segmented image data.

10. The method according claim 4, further comprising:
acquiring atlas data at the input of the medical processing system, the atlas data describing an image-based model of the anatomical structure,
wherein the determining the segmentation data comprises determining the segmentation data by matching the atlas data to the patient image data, wherein the matching applies an image fusion algorithm to the patient image data and the atlas data.

11. A non-transitory computer-readable program storage medium storing a program executable by an associated computer comprising a memory and a processor for performing a method of determining the position of an artifact in patient image data, the method comprising:
acquiring patient image data, the patient image data describing a set of tomographic slice images of an anatomical structure of an associated patient, wherein the tomographic slice images of the patient image data are described by color values;
determining, based on the patient image data and for each of a plurality of pairs of adjacent ones Of the tomographic slice images, a corresponding plurality of color value difference data sets describing differences in color values of image elements between the adjacent ones of the tomographic slice images, each selected color value difference data set being determined as differences by subtracting, for a corresponding selected pair of adjacent tomographic slice images, a color value of an element of a first one of the selected pair of adjacent tomographic slice images from a color value of an element of a second one of the selected pair of adjacent tomographic slice images;
determining for the plurality of color value difference data sets:
at least one of a corresponding plurality of positive difference data sets or a corresponding plurality of negative difference data sets, a selected positive difference data set relative to a corresponding selected color value difference data set describing a subset of the differences resulting from the subtracting of the color value of the element of the first one of the pair of adjacent tomographic slice images corresponding to the selected color value difference data set from the color value of the element of the second one of the selected pair of adjacent tomographic slice images corresponding to the selected color value difference data set and consisting of only differences having a positive value, and a selected negative difference data set relative to the corresponding selected color value difference data set describing a subset of the differences resulting from the subtracting of the color value of the element of the first one of pair of adjacent tomographic slice images corresponding to the selected color value difference data set from the color value of the element of the second one of the selected pair of adjacent tomographic slice images corresponding to the selected color value difference data set and consisting of only differences having a negative value;
determining, based on the at least one of the plurality of positive difference data sets or the plurality of negative difference data sets, smoothed difference data describing a smoothing of the differences contained in the at least one of the plurality of positive difference data sets or the plurality of negative difference data sets; and
determining the artifact position data by comparing the smoothed difference data with the at least one of the plurality of positive difference data sets or the plurality of negative difference data sets and determining a difference between the smoothed difference data and the at least one of the plurality of positive difference data sets or the plurality of negative difference data sets in accordance with the comparing, the artifact position data describing the position of the artifact in the patient image data using separately the plurality of positive difference data sets or the plurality of negative difference data sets in accordance with the determining of the plurality of positive difference data sets or the plurality of negative difference data sets.

12. A system for determining a position of an artifact in patient image data describing a set of tomographic slice images of an anatomical structure of an associated patient, the system comprising:
at least one medical imaging device, the at least one imaging device being operable to acquire the patient image data describing the set of tomographic slice images of the anatomical structure of the associated patient; and
at least one computer operably coupled with the at least one medical imaging device, the at least one computer being operable to:
acquire, from the at least one medical imaging device, the patient image data describing the set of tomographic slice images of the anatomical structure of the associated patient, wherein the tomographic slice images of the associated patient image data are described by color values;
determine, by the processor of the medical data processing system, based on the patient image data and for each of a plurality of pairs of adjacent ones of the tomographic slice images, a corresponding plurality of color value difference data sets describing differences in color values of image elements between the adjacent ones of the tomographic slice images, each selected color value difference data set being determined as differences by subtracting, for a corresponding selected pair of adjacent tomographic slice images, a color value of an element of a first one of the selected pair of adjacent tomographic slice images from a color value of an element of a second one of the selected pair of adjacent tomographic slice images;

determine, by the processor of the medical data processing system for the plurality of color value difference data sets:

at least one of a corresponding plurality of positive difference data sets or a corresponding plurality of negative difference data sets, a selected positive difference data set relative to a corresponding selected color value difference data set describing a subset of the differences resulting from the subtracting of the color value of the element of the first one of the pair of adjacent tomographic slice images corresponding to the selected color value difference data set from the color value of the element of the second one of the selected pair of adjacent tomographic slice images corresponding to the selected color value difference data set and consisting of only differences having a positive value, and a selected negative difference data set relative to the corresponding selected color value difference data set describing a subset of the differences resulting from the subtracting of the color value of the element of the first one of the pair of adjacent tomographic slice images corresponding to the selected color value difference data set from the color value of the element of the second one of the selected pair of adjacent tomographic slice images corresponding to the selected color value difference data set and consisting of only differences having a negative value;

determine, by the processor of the medical data processing system, based on the at least one of the plurality of positive difference data sets or the plurality of negative difference data sets, smoothed difference data describing a smoothing of the differences contained in the at least one of the plurality of positive difference data sets or the plurality of negative difference data sets; and determine the artifact position data by the processor of the medical data processing system by comparing the smoothed difference data with the at least one of the plurality of positive difference data sets or the plurality of negative difference data sets and determining a difference between the smoothed difference data and the at least one of the plurality of positive difference data sets or the plurality of negative difference data sets in accordance with the comparing, the artifact position data describing the position of the artifact in the patient image data using separately the plurality of positive difference data sets or the plurality of negative difference data sets in accordance with the determining of the plurality of positive difference data sets or the plurality of negative difference data sets.

* * * * *

UNITED STATES PATENT AND TRADEMARK OFFICE
CERTIFICATE OF CORRECTION

PATENT NO. : 10,628,963 B2
APPLICATION NO. : 16/066551
DATED : April 21, 2020
INVENTOR(S) : Pascal Bertram et al.

Page 1 of 1

It is certified that error appears in the above-identified patent and that said Letters Patent is hereby corrected as shown below:

On the Title Page

Item (54), "AUTOMATIC DETECTION OF AN ARTIFACT IN PATIENT IMAGE" should be changed to "AUTOMATIC DETECTION OF AN ARTIFACT IN PATIENT IMAGE DATA".

In the Claims

Column 21, Line 7 of Claim 7, "Housefield" should be changed to "Hounsfield".

Signed and Sealed this
Twenty-third Day of June, 2020

Andrei Iancu
*Director of the United States Patent and Trademark Office*